United States Patent [19]

Lokken

[11] 4,318,742

[45] Mar. 9, 1982

[54] ODONTOLOGIC COMPOSITIONS AND PREPARATION THEREOF

[75] Inventor: Oddvin Lokken, Rye, N.Y.

[73] Assignee: Solar Dental Co., Inc., North Miami Beach, Fla.

[21] Appl. No.: 79,380

[22] Filed: Sep. 27, 1979

Related U.S. Application Data

[63] Continuation-in-part of Ser. No. 966,605, Dec. 5, 1978, abandoned.

[51] Int. Cl.³ .......................... C08L 1/02; C08L 1/26; C08L 7/00; C08L 9/00
[52] U.S. Cl. .................... 106/35; 106/163 R; 106/191; 260/750; 260/751; 260/998.11; 525/207; 525/222; 525/223; 525/225; 523/120; 524/35; 524/45
[58] Field of Search .............. 106/35, 163 R, 197; 260/29.6 RW, 29.7 W, 17 R, 4, 998.11, 750, 751, 17.4 ST, 17.4 R, 17.4 BB, 28.5 R, 28.5 A; 525/207, 222, 223, 255

[56] References Cited

U.S. PATENT DOCUMENTS

| | | | |
|---|---|---|---|
| 2,273,425 | 2/1942 | Traylor | 260/30.8 R |
| 2,997,369 | 8/1961 | Eberhard et al. | 106/35 |
| 3,511,791 | 5/1970 | Puetzer et al. | 260/17.4 ST |
| 3,751,399 | 8/1973 | Lee et al. | 106/35 |
| 3,868,259 | 2/1975 | Keegan et al. | 106/35 |
| 3,868,260 | 2/1975 | Keegan et al. | 106/35 |
| 3,868,340 | 2/1975 | Keegan et al. | 106/35 |
| 3,878,138 | 4/1975 | Keegan et al. | 106/35 |
| 3,914,405 | 10/1975 | Shepherd et al. | 424/49 |
| 3,919,139 | 11/1975 | Keegan et al. | 106/35 |
| 3,936,402 | 2/1976 | Keegan et al. | 106/35 |
| 4,001,151 | 1/1977 | Keegan et al. | 106/35 |
| 4,108,823 | 8/1978 | Yoshimura et al. | 106/35 |

FOREIGN PATENT DOCUMENTS

| | | | |
|---|---|---|---|
| 550484 | 12/1957 | Canada | 106/35 |
| 902304 | 6/1972 | Canada | 106/35 |
| 2415333 | 10/1974 | Fed. Rep. of Germany | 106/35 |
| 2418125 | 8/1975 | Fed. Rep. of Germany | |

*Primary Examiner*—Allan Lieberman
*Attorney, Agent, or Firm*—Brooks, Haidt, Haffner & Delahunty

[57] ABSTRACT

Odontologic compositions suited for use as denture adhesives, the compositions containing a major amount of gum base and a quantity of a hydrophilic polymer to modify the adhesive properties of the gum base together with processes for producing such compositions.

10 Claims, No Drawings

ODONTOLOGIC COMPOSITIONS AND PREPARATION THEREOF

BACKGROUND OF THE INVENTION

This application is a continuation-in-part of my application Ser. No. 966,605 filed on Dec. 5, 1978, and now abandoned.

The present invention relates to odontologic compositions, and more particularly, it relates to compositions for use in association with dentures, as well as to methods for preparing such compositions.

Considerable advances have been made in the preparation of dental prostheses, and it is possible in the present state of the art to prepare dentures having a very satisfactory appearance. However, there has been some disagreement among dental authorities concerning fitting of dentures and the use of adjuvant compositions such as denture adhesives. One school of thought has held that no adjuvant composition should be used with dentures, and that such adjuvants tend to be substitutes for the proper fitting of the denture. Another school asserts that if it is possible to make the patient more comfortable through the use of adjuvant compositions, that such compositions should be utilized.

One of the strong reasons for the belief of some authorities that the use of dental adhesives is contraindicated is the failure of prior art compositions to meet the numerous performance criteria associated with such adhesives. The first and most apparent criterion is that any odontologic composition be non-toxic to the user, and the composition should also be non-irritating so that it can be tolerated indefinitely.

Clearly, the adhesive should not be readily soluble in fluids which are introduced into the oral cavity, including both indigenous fluids such as salivary secretions and exogenous fluids such as food and beverages. A second desirable property is a degree of adhesion which will serve to fix the prosthesis in its desired place with respect to the maxillary arch or to the inner surface of the mandible, or to both surfaces when the prosthesis is to replace both the upper and lower dentition.

While these properties are difficult to achieve, a further problem in such odontologic compositions is the necessity to provide sufficient cushioning for dynamic action in the composition, and such dynamic activity must of course not cause the composition to be forced out under the occlusal forces present during eating.

The G. D. Stafford article, "Dental Adhesives—A Review of Their Uses and Compositions", appearing in Dent. Practit. 21(1), 17 (September 1970) sets out some of the considerations and disadvantages in the use of a dental adhesive. A study of available denture adhesives is reported by Kapur in J. Pros. Dent. 18(6), 550 (December 1967). Kapur summarizes the results as showing that improved denture retention does not show a significant increase in masticatory performance and noted that mandibular denture retention significantly decreased after subjects had chewed foods or sipped liquids. Herlands et al, J. Pros. Dent. 10(2), 278 (1960), tested a new denture adhesive and concluded that denture adhesives should not be used when well-fitting dentures are tolerated by the patient.

U.S. Pat. 3,914,405 shows the use of hydrophilic polymers in cosmetic compositions and toothpastes. U.S. Pat. No. 3,621,079 shows the use of hydrophilic polymers prepared from acrylic ester monomers for use, inter alia, as a denture liner. Dental uses of hydrophilic polymers, and soft linings for dentures in particular, are shown by Sklover et al, Dental Dig., page 451 (October 1967) and in U.S. Pat. No. 3,808,686.

THE INVENTION

The present invention provides odontologic compositions which afford excellent adhesion of dentures to the surfaces of the oral cavity and at the same time do not adversely affect the oral tissues. These compositions are capable of withstanding the very high occlusal forces generated during mastication of foodstuffs and are nevertheless readily utilized by the wearer.

Briefly, the compositions of the present invention comprise a gum base and an hydrophilic polymer. The compositions in certain embodiments of the invention also contain auxiliary materials which improve the functioning of the adhesive in various uses and other auxiliary ingredients which improve the aesthetics and cosmetics of the compositions. The processes for preparing the compositions comprise heating the gum base, dispersing microfine hydrophilic polymer in a suitable vehicle, and mixing the heated gum base and dispersed hydrophilic polymer.

The gum base used in the present invention provides the adhesivity required and is utilized in a sufficient quantity to provide the essential adhesive properties. The gum bases used in preparing the present odontologic compositions contain as a principal ingredient gum latex solids, which when natural or of vegetable origin are generally obtained from exudates from various trees by coagulation or concentration of latices of the order Sapotaceae, Apocynaceae, Moraceae or Euphorbiaceae. They are derived from aqueous latices of chiefly polyisoprenoid materials. Generally, they are found to be insoluble in water, alcohol, acetone, or ether, but they are soluble in such liquids as chloroform or carbon disulfide.

The gum latex solids utilized herein include natural gum solids such as: chicle, chicle gum, zapota gum and the like obtained from the sapodilla tree, *Sapota achras*, and balata obtained from the tree *Mimusops globosa*, and can include jelutong and pontianak gums as well as synthetic gum bases. Generally, the gum base latices used herein contain less than about 50 percent water. The gum latex solids can be a mixture of various gums. Balata and chicle solids are preferred for use herein, and chicle is especially preferred.

Synthetic gum solids suitable for use in this invention include butadiene-styrene rubber, copolymers of isobutylene and isoprene (butyl rubber), paraffin (synthesized by Fischer-Tropsch process from carbon monoxide and hydrogen and removal of low molecular weight fractions and purified through activated charcoal), food grade petroleum wax and synthetic petroleum wax, polyethylene (MW 2,000–21,000), polyisobutylene (minimum molecular weight 37,000–Flory), polyvinyl acetate (minimum molecular weight 2,000).

Combinations of natural gum solids and synthetic gum solids can also be employed.

The gum solids can contain a variety of other materials to augment or modify their properties, as long as they are nontoxic, such as plasticizing materials of softeners to improve their handling and processing characteristics; tackifiers to alter their adhesive properties; antioxidants and preservatives to retard degradation, and flavoring agents, such as natural and artificial sweeners and fruit or mint flavors to improve taste. As taught further hereinafter, however, excessive amounts of such materials should be avoided because of their tendency to pick-up undesirable attributes, and especially in large quantities, they may interfere with adhesion, and may be leached or dissolved out of the composition.

Suitable plasticizing materials or softeners include: glycerol ester of partially dimerized rosin, glycerol ester of partially hydrogenated gum or wood rosin, glycerol ester of polymerized rosin, glycerol ester of gum rosin, glycerol ester of tall oil rosin, glycerol ester of wood rosin, lanolin methyl ester of rosin (partially hydrogenated), pentaerythritol ester of gum or wood resin, rice bran wax, stearic acid, sodium and potassium stearates.

Suitable tackifier resins include synthetic terpene resins such as polymers of α-pinene, β-pinene and or dipentene, natural terpene resins such as polymers of α-pinene (softening point minimum 155° C., determined by U.S.P. closed capillary method).

Suitable antioxidants and preservatives include butylated hydroxyanisole, butylated hydroxytoluene and paraaminobenzoic acid, and the like.

It should be understood that the term "gum base" as used in this specification means the combination of one or more natural of synthetic gums or rubber polymers together with, as desired or required, one or more plasticizing materials, tackifiers, antioxidants and preservatives.

The hydrophilic polymers contemplated herein are materials which have an affinity for water. Among the hydrophilic polymers found suitable for use in the practice of this invention are polymers and copolymers of methacrylic acid esters containing at least one hydroxyl group in the side chain, cellulosic polymers such as alphacellulose, sodium carboxymethyl cellulose, calcium sodium poly (vinyl methyl ether maleate). Other suitable hydrophilic, food-grade polymeric materials will readily suggest themselves to the person skilled in the art. The hydrophilic polymers used in the practice of this invention are in microfine form, that is, in the form of a powder, the particles of which are small. It is generally desirable that the particles are smaller than 250 mesh, and hydrophilic polymers of 325 mesh and smaller are preferred.

Among the preferred hydrophilic polymers used in the practice of this invention are polymers and copolymers of methacrylic acid esters containing at least one hydroxyl group in the side chain. In general, such hydrophilic polymers are prepared from monomers which can be represented by the formula

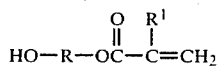

where R is a lower alkylene group and $R^1$ is a hydrogen or a lower alkyl group. Desirably R in the foregoing formula is an alkylene group containing two or three carbon atoms and $R^1$ is hydrogen or methyl. The molecular weights of such materials range upward from 250,000, and molecular weights of about 250,000 to 1,000,000 are preferred in certain embodiments.

There is extensive prior art knowledge concerning such hydrophilic polymers and their preparation. Better properties are obtained when the methacrylic ester polymer or copolymer contains some degree of cross-linking. This has the effect of providing further structure in the material. Acrylic and methacrylic diesters have been used for such purposes, and methacrylic acid and various derivatives thereof have also been used, either alone or in conjunction with the diesters. The actual preparation of such materials is set forth, for example, in U.S. Pat. No. 3,963,685 and in British Pat. Nos. 814,009 and 829,565.

Numerous other preparations of such hydrophilic polymers are set forth in the prior art, as instanced by U.S. Pat. Nos. Re 27,401; 4,083,264; 3,529,949; 3,551,556; and 3,780,003. It has been found in certain preferred embodiments of the present invention that polymers of 2-hydroxyethylmethacrylate (also known as "HEMA") give excellent results. The HEMA polymer properties are enhanced by the presence of a few weight percent of ethylene glycol dimethacrylate. Such cross-linking reduces the water swelling of the finished hydrophilic polymer.

As taught above, the gum base provides adhesion to to the composition, and it also provides body. As a result of the gum base, the compositions of the present invention have "plastic elasticity". They adapt themselves to the stresses and strains set up on the oral tissues. The dynamics of the compositions respond to the occlusal forces so that retention of the denture is greatly improved, and at the same time the wearer is comfortable and the tissues are not damaged. It is also believed that resorption of the bony structure is retarded or obviated. The gum latex is accordingly the major constituent of the present compositions.

The hydrophilic polymer serves to moderate and improve the properties of the gum base. If the quantity of hydrophilic polymer is too low, that is, substantially less than 1.5 percent of the composition, the composition is difficult to remove from the tissues and the surfaces of the dentures. When the quantity of hydrophilic polymer is too great, the desired "plastic elasticity" described above is lost. In fact, use of pure hydrophilic polymer or of a composition which is very high in hydrophilic polymer does not provide satisfactory results.

It has been attempted to utilize hydrophilic polymers in various sheet thicknesses but its intramolecular strength could not withstand the pressures generated under biting and similar occlusal forces. It is thus desirable that the hydrophilic polymer comprise not more than 35 percent of the composition. In certain preferred embodiments, the compositions of this invention contain from 1.5 to 20 percent of the hydrophilic polymers, and in especially preferred embodiments the quantity of hydrophilic polymer is from two to ten percent.

As taught above, the compositions according to this invention can also contain auxiliary ingredients to affect the physical or chemical properties of the compositions or to assist in their manufacture and auxiliary ingredients to provide the desired product aesthetics. While some of these auxiliaries may leach out or be changed during manufacture or use of the compositions of the invention, the hydrophilic polymer will remain and continue to perform its function.

Various vegetable gums, such as gum arabic, can be used to modulate the rheological properties of the compositions. Various pharmaceutical ingredients can be incorporated. Thus, antibiotics and antifungal agents can be added to prevent infection. Small quantities of topical anesthetic can be provided to improve comfort during initial fittings of the dentures. It is even possible to incorporate encapsulated materials or to carry such auxiliary materials in the hydrophilic polymer to provide a sustained release of the auxiliaries. Some vehicles, such as ethyl alcohol, can also be present in small quantities to facilitate preparation of the compositions. Antiviral and anticarcinogenic materials can also be incorporated. Various fluoride compounds can be added to the compositions of this invention to prevent caries when the user has a partial removable denture.

Aesthetic auxiliaries include colorings, flavorings, perfumes or other odorants, opacifiers and the like to improve the appearance of the compositions and to make them more pleasing to the user. Addition of small quantities of opacifier and coloring will give the compositions an appearance closely matching that of the user's gums, buccal surfaces, lingual surfaces, and palatal surfaces. Flavoring materials are added to make use of the denture adhesive compositions more pleasant and fragrance materials also create an estimable organoleptic impression. Thus, sugar, xylitol, glycerin or other agents can be readily incorporated into the compositions. Flavoring materials including natural essential oils and synthetic flavoring agents can also be employed.

These auxiliary materials are used in the quantities necessary to provide the desired effect. In the case of antibiotics or flavoring materials, the quantities utilized can be quite small. With opacifiers, coloring materials, and other ingredients, considerably greater quantities can be used. It is generally desirable that such auxiliary ingredients comprise less than 25 percent of the compositions, and in certain preferred embodiments, not more than 15 percent is utilized.

The compositions of the invention are prepared by first heating the gums or rubbers to improve their workability. The temperature utilized for this purpose are elevated above oral body temperature and desirably range from 100° to 150° F., depending upon the particular gum latex in use. Temperatures of 115° to 130° F. are preferably employed.

The hydrophilic polymer is in the form of finely divided particles or powder. In fact, the quantity of hydrophilic polymer used depends to some extent on the particle size of the polymer. It is frequently found that the properties of the compositions can be obtained with a lesser usage of hydrophilic polymer when the polymer is more finely comminuted.

The hydrophilic polymer is dispersed in a vehicle. The vehicles used are those which are acceptable for oral ingestion, that is, they are non-toxic and innocuous materials. One especially preferred vehicle is ethyl alcohol.

The vehicles containing the hydrophilic polymer and the heated gum base are then combined in a mixer. It is preferable to add the hydrophilic polymer to the plasticizer and softer components before combining this mixture with the rubbers and gums. The hydrophilic polymer is then thoroughly and uniformly dispersed in the gum base. The auxiliary ingredients can be added to the gums or rubber prior to addition of the hydrophilic polymer or the auxiliaries can be added with or after the hydrophilic polymer and vehicle. The mode of adding the auxiliaries will depend upon their physical nature. When the auxiliaries are in relatively small quantities and it will be difficult to distribute them through the composition, they are preferably added to the gums with the hydrophilic polymer and vehicle.

The compositions obtained according to this invention do not dissolve in the user's salivary and other oral secretions; they are non-toxic and non-irritating. They greatly improve the ability of the user to maintain his dentures in place and they readily conform to the surfaces of the mouth and the dentures. With auxiliary ingredients, the other properties can also be enhanced to provide an attractive appearance and satisfying use over an extended period of time. The denture adhesive compositions can also be readily removed from the oral tissues and from the dentures, so that the dentures can be cleaned as desired and then replaced. The denture adhesive compositions of this invention provide a resilient cushion between the oral tissue and the denture allowing for dynamic action yet withstanding occlusal forces. This resilient cushion minimizes trauma and irritation to the oral tissue during mastication. The denture adhesive compositions may be used particularly for patients with damaged oral tissue and those with poor mandibular ridges and bone breakdown or changes. While the present compositions can be left on the dentures and in the mouth for extended periods of time, it is presently believed that the dentures should be removed and the compositions replaced once a day or more frequently depending on the oral hygiene requirements.

The following Examples are given to illustrate embodiments of the invention as it is presently preferred to practice it. It will be understood that these Examples are illustrative, and the invention is not to be considered as restricted thereto except as indicated in the appended claims.

All parts, percentages, proportions, and ratios herein are by weight unless otherwise indicated.

EXAMPLE 1

A hydrophilic polymer obtained from HEMA monomer cross-linked with about one percent of ethylene glycol dimethacrylate is dispersed in an equal quantity of ethyl alcohol. The material used in this Example is sold under the name "Hydron N325". A gum latex chicle is heated to about 120° F. and to 85 g of this latex is added 7 g of the alcohol/hydrophilic polymer dispersion, 4 g of starch, and 4 g of gum tragacanth. Thereafter, about one gram of flour, coloring, and zinc oxide inert opacifier is added, and the ingredients are thoroughly mixed for 20 minutes.

At the end of the 20-minute time period, the composition is removed from the mixing container. A denture user having a mandibular plate utilizes a sample of the composition. It is found to provide excellent adhesion and enables the user to eat and drink normally during a 24-hour period without any difficulty.

EXAMPLE 2

(a) To a mixture containing the following ingredients in the amounts indicated

| Ingredient | Parts |
|---|---|
| Sapotaceae chicle gum | 35 |
| Polyvinyl acetate | 3 |
| Copolymer of isobutylene and isoprene (butyl rubber) | 8 | are added 7 parts of a terpene oil consisting of polymers of α-pinene, β-pinene and/or dipentene. The combined mixture is permitted to stand at room temperature in a closed container for 24 hours. Then the mixture is heated to 120° F. while agitating same and a doughy mix is obtained.

(b) Ethyl alcohol (20% by volume) is added in an amount sufficient to dissolve a mixture of 7 parts of glycerol ester of rosin, 4 parts of lecithin and 3 parts of alpha-cellulose hydrophilic polymer and bring the mixture to a syrupy consistency.

(c) A mixture of the following ingredients in the amounts indicated as prepared:

| Ingredient | Parts (per 100 parts total composition) |
|---|---|
| Petrolatum | 7 |
| Paraffin (FDA grade) | 3 |
| Candelilla wax | 6 |
| Hydrofol saturated animal fat | 4 |
| Sodium stearate | 3 |
| Corn oil | 10 | is heated to about 120° F. until all the solid materials are dissolved.

Components (a) and (b), above, are first placed in a blender and admixed at liquefying speed while maintaining the temperature of the mixture at 120° F. Then component (c) is added to the blender and admixed at liquefying speed at a temperature of 120° F. If desired, coloring and a preservative such as para-aminobenzoic acid are added at this stage in small amount. Upon cooling, an adhesive paste composition is obtained which when applied to dentures provides excellent adhesion, good adaptability to the tissue, good conformability, and the adhesive can be readily peeled or removed from the tissue and the denture.

EXAMPLE 3

A denture adhesive composition is prepared essentially as described in Example 2, except that instead of adding three (3) parts of alpha-cellulose to component (b) of Example 2, three (3) parts of poly(vinyl methyl ether-maleate) hydrophilic polymer is added to the component (c).

EXAMPLE 4

A denture adhesive composition is prepared essentially as described in Example 3, except that sodium carboxymethyl cellulose hydrophilic polymer is substituted for the poly (vinyl methyl ether-maleate) of Example 3.

EXAMPLE 5

A denture adhesive composition is prepared essentially as described in Example 2, except that the "Hydron N325" hydrophilic polymer of Example 1 is substituted for the alpha cellulose of Example 2.

It should be understood that the examples illustrate the preparation of a paste-like composition. The consistency of the denture adhesive composition may be readily varied by modifying the amounts and types of the various gums, softeners, and corn-oil ingredients employed. Thus, for example, to obtain a less stringy and less sticky composition capable of being tube-dispensed, the amount of butyl rubber used can be reduced and the amount of chicle gum increased; and if the adhesive composition is too hard, the amount of natural and/or synthetic gums can be reduced and the amount of softeners or plasticizers (e.g. corn oil and the other constituents of component (c), above) can be increased. Modification of the formulation can thereby be made to obtain the desired degree of adhesivity (modulating the terpene resin tackifiers), consistency, flowability, and cohesiveness (tendency of the composition to stay together and be partitioned).

A softer more tube-dispensable formulation is illustrated by the following example.

EXAMPLE 6

(a) The following ingredients in the amounts indicated

| Ingredients | Parts |
|---|---|
| Sapataceae chicle gum | 30 |
| Polyvinyl acetate | 7 |
| Butyl rubber (isoprene/isobutylene copolymer) | 5 |
| Terpene oil as in Example 2 | 7 | are combined in a vessel, permitted to stand for 24 hours and then heated to 120° F. while agitating same. A doughy mix is obtained.

(b) A mixture of 4 parts of gum arabic (acacia U.S.P.), 7 parts of a glycerol ester of rosin, and 4 parts of lecithin are dispersed in sufficient ethyl alcohol (20% by volume) to obtain a syrupy consistency.

(c) The following ingredients in the stated amounts are combined and heated to about 120° F. until all the solid materials are disolved.

| Ingredients | Parts |
|---|---|
| Parafin | 2 |
| Candelilla Wax | 3 |
| Hydrofol saturated animal fat | 2 |
| Sodium stearate | 2 |
| Corn oil | 2 |
| Petrolatum | 17 |
| Hydron N 325 of Example 1 | 8 |

Components (a) and (b) are placed in a blender and admixed at liquefying speed while maintaining the temperature of the mixture at 120° F. Then component (c) is added, blended at liquefying speed at a temperature of 120° F. until uniformly admixed.

The adhesive denture composition can be readily partitioned and is of a consistency permitting it to be dispensed from a tube having a normal "toothpaste" orifice size.

In a similar manner, denture adhesive compositions are made substituting powdered alpha-cellulose or calcium sodium poly (vinyl methyl ether maleate) for the Hydron used in this Example. If desired, a combination of two or more hydrophilic polymers may also be used.

It should be understood also that these examples are representative of the wide variety of non-toxic ingredients which can be included in the compositions for the desired physiologic and cosmetic effects.

What is claimed is:

1. A denture-adhesive composition containing a major amount of a water-insoluble natural or synthetic polymer gum base selected from the group consisting of chicle, chicle gum, zapota gum, balata, butadiene-styrene rubber, butyl rubber, food grade petroleum wax, synthetic petroleum wax, polyethylene having a molecular weight of from about 2000 to 21,000, polyisobutylene having a minimum molecular weight of about 37,000, polyvinylacetate having a minimum molecular weight of about 2000, and mixtures of two or more of same and from about 1½ to 35 percent by weight based on the total weight of the composition of a hydrophilic polymer initially of a fine particle size, said hydrophilic polymer being selected from the group consisting of polymers and copolymers of methacrylic acid esters containing at least one hydroxyl group in the side chain, alpha-cellulose, sodium carboxy methyl cellulose, and calcium sodium poly(vinyl methyl ether maleate), and said hydrophilic polymer being sufficient to permit removal of the composition from oral tissue and the denture.

2. A denture adhesive composition as defined in claim 1 wherein said hydrophilic polymer is alpha-cellulose or an alkali-metal carboxy methyl cellulose.

3. A denture adhesive composition as defined in claim 1 wherein said hydrophilic polymer is a polymer of an hydroxyalkyl acrylate or methacrylate.

4. A denture adhesive as defined in claim 3 where said polymer is derived from 2-hydroxyethyl methacrylate.

5. A denture adhesive composition as defined in claim 3 wherein the base hydrophilic polymer is prepared from a monomer having the formula

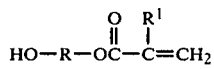

wherein R is a lower alkylene group having from two to four carbon atoms and $R^1$ is hydrogen or a lower alkyl group having from one to three carbon atoms.

6. A composition according to claim 1 wherein there is additionally present at least one auxiliary agent to provide a physical or aesthetic effect.

7. A composition according to claim 1 wherein the quantity of hydrophilic polymer is from about 1.5 to about 20 percent.

8. A composition according to claim 5 wherein the hydrophilic polymer contains a small quantity of a diester sufficient to cross-link the polymer.

9. A composition according to claim 1 wherein the particle size of the hydrophilic polymer is about 250 mesh or smaller.

10. A process for removably securing a dental prosthesis to a surface of an oral cavity which comprises applying to a surface of dental prosthesis or oral cavity a denture adhesive composition containing a major amount of a water-insoluble natural or synthetic polymer gum base selected from the group consisting of chicle, chicle gum, zapota gum, balata, butadiene-styrene rubber, butyl rubber, food grade petroleum wax, synthetic petroleum wax, polyethylene having a molecular weight of from about 2000 to 21,000, polyisobutylene having a minimum molecular weight of about 37,000, polyvinylacetate having a minimum molecular weight of about 2000, and mixtures of two or more of same and from about 1½ to 35 percent by weight based on the total weight of the composition of a hydrophilic polymer initially of a fine particle size said hydrophilic polymer being selected from the group consisting of polymers and copolymers of methacrylic acid esters containing at least one hydroxyl group in the side chain, alpha-cellulose, sodium carboxy methyl cellulose, and calcium sodium poly(vinyl methyl ether maleate), and said hydrophilic polymer being sufficient to permit removal of the composition from oral tissue and the denture.